United States Patent [19]

Skinner et al.

[11] 4,299,840

[45] Nov. 10, 1981

[54] METHOD FOR REPELLING TICKS AND INSECTS

[75] Inventors: Wilfred A. Skinner, Portola Valley, Calif.; Ulrich Rosentreter, Wunstorf, Fed. Rep. of Germany; Thomas E. Elward, Palo Alto, Calif.

[73] Assignee: SRI International, Menlo Park, Calif.

[21] Appl. No.: 157,521

[22] Filed: Jun. 9, 1980

[51] Int. Cl.$^3$ .............................................. A01N 43/36
[52] U.S. Cl. ............................ 424/274; 424/DIG. 10
[58] Field of Search .................. 424/274; 260/326.5 R

[56] References Cited

U.S. PATENT DOCUMENTS 3,085,931  4/1963  Darlington ........................ 424/274
4,122,170  10/1978  Rajadhyaksha ............ 424/DIG. 10

OTHER PUBLICATIONS

Ladea; E. A. vol. 73 (1970) #102083d.

*Primary Examiner*—Allen J. Robinson
*Attorney, Agent, or Firm*—Donovan J. De Witt

[57] ABSTRACT

Process for repelling ticks and other biting insects comprising topically administering to humans or to domesticated animals a composition comprising at least one active compound selected from the group made up of alkylated pyrrolidones and alkylated pyrrolidenones.

8 Claims, No Drawings

METHOD FOR REPELLING TICKS AND INSECTS

BACKGROUND OF THE INVENTION

The principal insect repellents employed at the present time for reducing the population of ticks and other biting insect pests on the skin are DEET (N,N-diethyl-m-toluamide) and Indalone (butopyronoxyl). It is an object of this invention to provide other insect repellent compositions having repellent qualities which are superior to those of DEET and Indalone particularly at low concentrations on the skin.

SUMMARY OF THE INVENTION

It has been found that the foregoing and other objects of this invention can be met by the use of alkylated pyrrolidones and alkylated pyrrolidenones of the type defined below by formulae I, II or III. Said compounds, or compositions containing the same, when topically applied to the human skin or to the hair or hide portions of a domesticated animal in effective amounts are believed to be suitable for use as repellent compounds which are effective against biting arthropods such as ticks.

The active compounds employed in a practice of the present invention comprises those selected from one or another of the following Groups I, II or III:

I. A compound of the formula

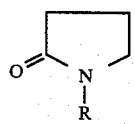

wherein R represents an alkyl group of from about 6 to 12 carbon atoms;

II. A compound of the formula

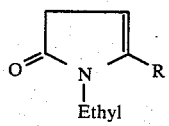

wherein R represents an alkyl group of from about 4 to 12 carbon atoms; and

III. A compound of the formula

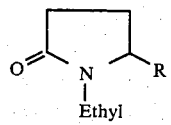

wherein R represents an alkyl group of from about 6 to 12 carbon atoms.

Methods for preparing the compounds belonging to the foregoing Groups I, II and III are set forth below in Examples 1, 2 and 3, respectively. Thus, the compound of Group I which forms the subject of Example 1 is 1-decyl-azacylclopentan-2-one. Here R represents the decyl group. Example II discloses the preparation of the Group II compound 1-ethyl-5-octylazacyclopent-5-ene-2-one. Here R is represented by an octyl group. Example III discloses the preparation of the Group III compound 1-ethyl-5-octyl-azacyclopentan-2-one where R is octyl. Compounds which are analogous to those of Examples 1, 2 and 3 can be prepared in a fashion generally similar to that disclosed in the following Examples, but with the use of starting materials containing the desired alkyl groups.

EXAMPLE 1

1-Decyl-azacyclopentan-2-one 22.1 g 1-Bromodecane (0.1 mol), 8.5 g (0.1 mol) of 2-pyrrolidone and 11.2 g (0.1 mol) of potassium tert-butylate were stirred in 100 ml of absolute DMSO for one hour. The DMSO was removed under reduced pressure, the residue taken up with diethyl ether, and washed with water (2 times). After drying with anhydrous $MgSO_4$ and evaporating, the residue was distilled in vacuo. A first fraction, boiling between 140° and 147° C./1.2 mm Hg was discarded. The second fraction 17.4 g of pure product, b.p. 148° C./1.2 mm Hg.

EXAMPLE 2

1-Ethyl-5-octylazacyclopent-5-ene-2-one

A solution of octylmagnesium bromide was prepared by dropping 34.2 g (0.177 mol) of 1-bromoctane in 10 ml of diethyl ether into 6.5 g (0.268 mol) of magnesium in 10 ml of diethyl ether and refluxing for three hours. The solution of the Grignard reagent was transferred under nitrogen to the dropping funnel of a 150 ml three-necked flask additionally fitted with a reflux condenser, a magnetic stirrer and a nitrogen outlet and containing a solution of 15 g (0.118 mol) of N-ethyl-succinimide in 50 ml of absolute tetrahydrofuran. The Grignard reagent was added over a period of two hours. The reaction mixture with the precipitated alcoholate was allowed to stand at room temperature for two days. The suspension was poured into a mixture of ice and 10% $H_2SO_4$. After separation of the organic layer, the aqueous phase was extracted with diethyl ether (2 times). The combined organic phases were washed with saturated $NaHCO_3$. After drying with anhydrous $Na_2SO_4$ and removing the solvent under reduced pressure, the residue was distilled with a Kugelrohr in vacuo to give 10 g of a yellow oil, 120° C. air bath temperature/0.9 mm Hg. A second fractionated distillation over a Vigreux column yielded 6.6 g pure product, b.p. 130° C./1.0 mm Hg.

EXAMPLE 3

1-Ethyl-5-octyl-azacyclopentan-2-one 5.3 g 1-Ethyl-5-atylazacyclopent-5-ene-2-one (0.0238 mol) in 25 ml of ethanol was hydrogenated under normal pressure with 0.5 g of 10% palladium on charcoal as catalyst. After the uptake of hydrogen was completed, the catalyst was filtered off, the solvents evaporated, and the residue distilled to give 5 g of product, b.p. 130° C./0.9 mm Hg.

Using the general methods taught above in Examples 1, 2 and 3, other alkylated pyrrolidones and alkylated pyrrolidenones were prepared as indicated in the following table wherein the compounds are segregated into Groups I, II or III:

TABLE 1

| | b.p. (0.5 mm) | Yield (%) | I.R. (cm$^{-1}$) | | Analysis | | | |
|---|---|---|---|---|---|---|---|---|
| Group I | | | | | | | | |
| Compound R Group | | | | | | | | |
| Octyl | 110 | 85 | Amide 1690 | calc. found | C 73.05 C 72.86 | H 11.75 H 11.64 | N 7.10 N 7.11 | |
| Decyl | 122 | 78 | Amide 1690 | calc. found | C 74.61 C 74.49 | H 12.08 H 11.94 | M 6.21 N 6.21 | |
| Dodecyl | 150 | 91 | Amide 1690 | calc. found | C 75.83 C 75.96 | H 12.33 H 12.59 | N 5.53 N 5.46 | |
| Group II | | | | | | | | |
| Compound R Group | | | | | | | | |
| Butyl | 86 | 36.5 | Amide 1720 Double bond 1670 | calc. found | C 71.81 C 71.42 | H 10.25 H 10.16 | N 8.37 N 8.38 | |
| Pentyl | 94 | 39 | Amide 1720 Double bond 1670 | calc. found | C 72.89 C 73.15 | H 10.56 H 10.74 | N 7.73 N 7.43 | |
| Hexyl | 110 | 31 | Amide 1720 double bond 1670 | calc. found | C 73.80 C 73.66 | H 10.84 H 10.64 | N 7.17 N 7.14 | |
| Heptyl | 118 | 36 | Amide 1720 Double bond | calc. found | C 74.59 C 74.41 | H 11.07 H 11.04 | N 6.69 N 6.68 | |
| Octyl | 125 | 25 | Amide 1720 Double bond | calc. found | C 75.28 C 75.34 | H 11.28 H 11.33 | N 6.27 N 6.18 | |
| Decyl | 142 | 29 | Amide 1720 Double bond 1670 | calc. found | C 76.44 C 76.25 | H 11.63 H 11.42 | N 5.57 N 5.29 | |
| Group III | | | | | | | | |
| Compound R Group | | | | | | | | |
| Hexyl | 110 | 89 | Amide 1690 | calc. found | C 73.04 C 73.26 | H 11.75 H 11.97 | N 7.10 N 6.99 | |
| Octyl | 120 | 94 | Amide 1690 | calc. found | C 74.61 C 74.94 | H 12.08 H 12.09 | N 6.21 N 6.11 | |
| Decyl | 154 | 90 | Amide 1690 | calc. found | C 75.83 C 76.07 | H 12.33 H 12.44 | N 5.33 N 5.41 | |

In order to test the efficacy of the foregoing Group I, Group II and Group III compounds, along with that of DEET and Indalone in repelling ticks, each compound was subjected to the procedures described in the following Tick Repellent Assay:

This assay is designed to take advantage of the natural inclination of unfed ticks to climb upward. *Rhipicephalus sanguineus*, the brown dog tick, is the test anthropod.

Test materials are weighed, dissolved in ethanol, and 0.15 ml of the solution is applied to a disk. The disks are cut from No. 3 Whatman filter paper and are 2.9 cm in diameter. One disk is used per compound per treatment level. Treated disks are kept under a hood and allowed to dry for 24 hours before use.

Disks are then inserted in drilled-out vial caps so that the treated side faces down when the cap is placed on the test chamber. The test chamber is a 7-dram polystyrene vial (25×52 mm) with an untreated disk glued on the drilled-out bottom. Fifteen holes are punched in both disks on the chamber. Twenty unfed adult brown dog ticks (10 male and 10 female) sorted 24 hours before use, are placed in each test chamber. The chambers are held with the treated end upright under a hood and slightly elevated on tongue depressors. Four hours later, when the ticks have ceased wandering, the chamber is observed and the number of ticks that have settled on the treated surface are counted. The results are expressed in the percentage of ticks repelled from the treated surface. The maximum test level is 1.0 mg/cm$^2$ and the dose increments are 0.18 log intervals.

The data obtained by subjecting the Group I, II and III compounds, as well as DEET, Indalone and the controls to the foregoing Tick Repellent Assay method are set forth in the following table:

TABLE 2

| | Compound No. | Average % Repellency at Test Level mg/cm$^2$* | | | | |
|---|---|---|---|---|---|---|
| | | 1.0 | .66 | .44 | .29 | .19 |
| Group I | | | | | | |
| Compound R Group | | | | | | |
| Octyl | 1. | | | 78 | 25 | 20 |
| Decyl | 2. | | | 25 | | |
| Dodecyl | 3. | | | 20 | | |
| Group II | | | | | | |
| Compound R Group | | | | | | |
| Octyl | 4. | | | 98 | 82 | 47 |
| Decyl | 5. | | | 98 | 77 | 20 |
| Hexyl | 6. | | | 100 | 92 | 63 |
| Pentyl | 7. | | | 60 | | |
| Heptyl | 8. | | | 95 | | |
| Butyl | 9. | | | 25 | | |
| Group III | | | | | | |

TABLE 2-continued

| | Compound No. | Average % Repellency at Test Level mg/cm²* | | | | |
|---|---|---|---|---|---|---|
| | | 1.0 | .66 | .44 | .29 | .19 |
| Compound R Group | | | | | | |
| Octyl | 10. | | | 75 | 55 | |
| Decyl | 11. | | | 40 | | |
| Hexyl | 12. | | | 25 | | |
| DEET | | 96 | 54 | 32 | | |
| Indalone | | 98 | 83 | 48 | | |
| Solvent Control | 7% | | | | | |
| Non Treated Control | 9% | | | | | |

*The solutions of the active compound used to impregnate the filter paper had strengths of 0.8%, 1.2%, 1.9%, 2.9% and 4.4% to obtain the test levels of 0.19, 0.29, 0.44, 0.66 and 1.00 mg/cm², respectively.

The compounds employed in accordance with this invention to repell ticks and other small biting insects are liquids which are insoluble in water and readily soluble in organic solvents such as methanol, ethanol, isopropanol, acetone, methylene chloride, the various Tweens, DMSO, ethylene glycol, propylene glycol, polyethylene glycol and glycerin, for example.

The insect repellent compositions of the present invention contain an amount of the active alkylated pyrrolidones and alkylated pyrrolidenones which, in the form said composition is applied, will provide the desired level of insect repellency. For any given active compound the optimum amounts to be employed will vary from one insect to another as well as with the environmental conditions and the nature of the vehicle associated with the active compound. For example, in the control of ticks good results can be obtained with compositions which are adapted to provide a concentration on the skin of from about 0.05 mg of the active compound per square centimeter of skin surface (0.05 mg/cm²) to about 1 milligram per square centimeter, or even higher. For the treatment of dogs and other domestic animals these same ranges are meaningful. However good results can also be obtained at levels such, for example, as those which can be provided by the use of a collar which has been treated with active compounds in such a fashion that said compounds are gradually released to adjacent hair and hide portions of the animal. In one manner of formulating compositions which are useful in combating attack by ticks or other small biting insects the active compounds disclosed herein can be dissolved in a solvent vehicle which readily evaporates following topical application of the solution. Again, useful compositions of the present invention can be formulated by employing the active compounds in connection with relatively high boiling liquids such as vegetable oils or highly treated, white, odorless, non-viscous mineral oil fractions. Solutions of this character are adapted to be employed either as hand-applied liquid compositions or in the form of aerosol spray compositions. White the invention has been described herein in terms of its utility in connection with repelling ticks, the invention is believed to be similarly useful in connection with repelling mosquitoes, biting flies and the like.

We claim:

1. A process for repelling ticks and other small biting insects from the human skin or the hide portions of domestic animals which comprises administering to said skin or hide portions a solution of an active compound selected from the group consisting of those having the formula:

I. Compounds of the formula

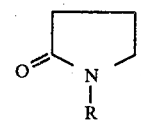

wherein R represents an alkyl group of from about 6 to 12 carbon atoms;

II. Compounds of the formula

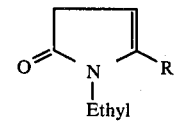

wherein R represents an alkyl group of from about 4 to 12 carbon atoms; and

III. Compounds of the formula

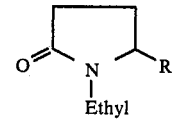

wherein R represents an alkyl group of from about 6 to 12 carbon atoms,
said solution being of such strength as to provide the treated skin or hide portions with from about 0.05 mg/cm² to about 1.0 mg/cm² of said active compound.

2. The process of claim 1 wherein the active compound is one of the Group I type in which R is octyl.

3. The process of claim 1 wherein the active compound is one of the Group II type in which R is pentyl.

4. The process of claim 1 wherein the active compound is one of the Group II type in which R is hexyl.

5. The process of claim 1 wherein the active compound is one of the Group II type in which R is heptyl.

6. The process of claim 1 wherein the active compound is one of the Group II type in which R is octyl.

7. The process of claim 1 wherein the active compound is one of the Group II type in which R is decyl.

8. The process of claim 1 wherein the active compound is one of the Group III type in which R is octyl.

* * * * *